(12) United States Patent
Pfutzner et al.

(10) Patent No.: US 12,378,882 B2
(45) Date of Patent: Aug. 5, 2025

(54) METHOD FOR PERFORMING RAMAN SPECTROSCOPY WITHIN A LOGGING WHILE DRILLING INSTRUMENT

(71) Applicant: Schlumberger Technology Corporation, Sugar Land, TX (US)

(72) Inventors: Harold Pfutzner, Richmond, TX (US); Bastian Sauerer, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 250 days.

(21) Appl. No.: 18/065,687

(22) Filed: Dec. 14, 2022

(65) Prior Publication Data

US 2023/0114341 A1     Apr. 13, 2023

Related U.S. Application Data

(62) Division of application No. 15/978,322, filed on May 14, 2018, now Pat. No. 11,530,611.

(51) Int. Cl.
*E21B 49/10* (2006.01)
*E21B 17/10* (2006.01)
(Continued)

(52) U.S. Cl.
CPC .......... *E21B 49/10* (2013.01); *E21B 17/1078* (2013.01); *E21B 47/01* (2013.01);
(Continued)

(58) Field of Classification Search
CPC ...... E21B 49/10; E21B 17/1078; E21B 47/01; E21B 47/017; E21B 47/0175;
(Continued)

(56) References Cited

U.S. PATENT DOCUMENTS

| | | | |
|---|---|---|---|
| 5,475,309 A | * | 12/1995 | Hong ............... E21B 47/013 324/333 |
| 5,517,024 A | | 5/1996 | Mullins et al. |

(Continued)

FOREIGN PATENT DOCUMENTS

| | | | | |
|---|---|---|---|---|
| CN | 105044077 A | * | 11/2015 | ............ G01N 21/65 |
| WO | 2004003506 A3 | | 5/2004 | |

(Continued)

OTHER PUBLICATIONS

Liu, Zhengfan, Lori A. Hathon, and Michael T. Myers. "Characterization of thermal maturity and organic material type With Raman Spectroscopy in shale reservoirs." SPWLA Annual Logging Symposium. SPWLA, 2017. (Year: 2017).*

(Continued)

*Primary Examiner* — Michelle M Iacoletti
*Assistant Examiner* — Noah J. Haney
(74) *Attorney, Agent, or Firm* — Jeffrey D. Frantz

(57) ABSTRACT

A downhole tool has a tool body with an outer diameter equal to a borehole diameter, at least one cavity formed in and opening to an outer surface defining the outer diameter of the tool body, a light source, a filter, and a light detector (Continued)

mounted in the at least one cavity, and a window disposed at the opening of the at least one cavity, wherein the window encloses the cavity.

17 Claims, 8 Drawing Sheets

(51) Int. Cl.
| | |
|---|---|
| *E21B 47/01* | (2012.01) |
| *E21B 47/017* | (2012.01) |
| *E21B 49/00* | (2006.01) |
| *G01J 3/02* | (2006.01) |
| *G01J 3/12* | (2006.01) |
| *G01J 3/18* | (2006.01) |
| *G01J 3/44* | (2006.01) |
| *G01N 21/65* | (2006.01) |
| *G01N 33/24* | (2006.01) |
| *G01V 8/02* | (2006.01) |

(52) U.S. Cl.
CPC ........ *E21B 47/017* (2020.05); *E21B 47/0175* (2020.05); *E21B 49/00* (2013.01); *G01J 3/0286* (2013.01); *G01J 3/0291* (2013.01); *G01J 3/18* (2013.01); *G01J 3/44* (2013.01); *G01J 3/4412* (2013.01); *G01N 21/65* (2013.01); *G01N 33/24* (2013.01); *G01N 33/241* (2013.01); *G01V 8/02* (2013.01); *G01J 3/0264* (2013.01); *G01J 2003/1208* (2013.01)

(58) Field of Classification Search
CPC ....... E21B 49/00; G01J 3/0286; G01J 3/0291; G01J 3/18; G01J 3/44; G01J 3/4412; G01J 3/0264; G01J 2003/1208; G01N 21/65; G01N 33/24; G01N 33/241; G01V 8/02
USPC ........................................................ 356/301
See application file for complete search history.

(56) References Cited

U.S. PATENT DOCUMENTS

| | | | | |
|---|---|---|---|---|
| 5,912,459 A * | 6/1999 | Mullins | ................ | E21B 47/002 |
| | | | | 250/269.1 |
| 6,666,285 B2 | 12/2003 | Jones | | |
| 8,172,009 B2 | 5/2012 | Hall | | |
| 2006/0065394 A1 | 3/2006 | Clark | | |
| 2007/0171414 A1 | 7/2007 | Vannuffelen | | |
| 2008/0111064 A1 | 5/2008 | Andrews | | |
| 2011/0057656 A1* | 3/2011 | Tchakarov | .............. | E21B 10/00 |
| | | | | 324/369 |
| 2013/0270011 A1* | 10/2013 | Akkurt | .................. | E21B 49/088 |
| | | | | 175/58 |
| 2014/0208826 A1* | 7/2014 | Larter | .................... | G01N 11/00 |
| | | | | 356/70 |
| 2014/0245827 A1 | 9/2014 | Pope | | |
| 2014/0251690 A1 | 9/2014 | Simon | | |
| 2014/0326506 A1* | 11/2014 | DiFoggio | .............. | E21B 10/567 |
| | | | | 175/39 |
| 2015/0090443 A1* | 4/2015 | Bryndzia | ............ | G01N 33/241 |
| | | | | 166/250.01 |
| 2015/0218940 A1* | 8/2015 | Pelletier | ................ | E21B 49/005 |
| | | | | 175/41 |
| 2016/0273309 A1 | 9/2016 | Maher | | |
| 2016/0349174 A1 | 12/2016 | Washburn | | |
| 2017/0329045 A1* | 11/2017 | Myers | .................. | G01B 11/303 |
| 2019/0345822 A1 | 11/2019 | Pfutzner | | |

FOREIGN PATENT DOCUMENTS

| | | | | |
|---|---|---|---|---|
| WO | WO-2013100770 A2 * | 7/2013 | ........... | E21B 47/123 |
| WO | WO-2014022757 A1 * | 2/2014 | ........... | E21B 49/005 |
| WO | WO-2015188922 A2 * | 12/2015 | ............. | C30B 29/04 |
| WO | 2018156527 A1 | 8/2018 | | |

OTHER PUBLICATIONS

Schito, Andrea, et al. "Diagenetic thermal evolution of organic matter by Raman spectroscopy." Organic Geochemistry 106 (2017): 57-67. (Year: 2017).*
Khatibi, Seyedalireza, et al. "Evaluating the impact of mechanical properties of kerogen on hydraulic fracturing of organic rich formations." SPE Canada Unconventional Resources Conference ?. SPE, 2018. (Year: 2018).*
Sauerer, Bastian, et al. "Fast and accurate shale maturity determination by Raman spectroscopy measurement with minimal sample preparation." International Journal of Coal Geology 173 (2017): 150-157. (Year: 2017).*
Spotl, Christoph, David W. Houseknecht, and Robert C. Jaques. "Kerogen maturation and incipient graphitization of hydrocarbon source rocks in the Arkoma Basin, Oklahoma and Arkansas: a combined petrographic and Raman spectrometric study." Organic Geochemistry 28.9-10 (1998): 535-542. (Year: 1998).*
Schmidt, J. S., R. Hinrichs, and C. V. Araujo. "Maturity estimation of phytoclasts in strew mounts by micro-Raman spectroscopy." International Journal of Coal Geology 173 (2017): 1-8. (Year: 2017).*
Kelemen, S. R., and H. L. Fang. "Maturity trends in Raman spectra from kerogen and coal." Energy & fuels 15.3 (2001): 653-658. (Year: 2001).*
Mumm, Andreas Schmidt, and Sedat Ä°nan. "Microscale organic maturity determination of graptolites using Raman spectroscopy." International Journal of Coal Geology 162 (2016): 96-107. (Year: 2016).*
Khatibi, Seyedalireza, Mehdi Ostadhassan, and Azadeh Aghajanpour. "Raman spectroscopy: an analytical tool for evaluating organic matter." J Oil Gas Petrochem Sci 1.1 (2018): 28-33. (Year: 2018).*
Khatibi, Seyedalireza, et al. "Raman spectroscopy to study thermal maturity and elastic modulus of kerogen." International Journal of Coal Geology 185 (2018): 103-118. (Year: 2018).*
Bonoldi, Lucia, Lea Di Paolo, and Cristina Flego. "Vibrational spectroscopy assessment of kerogen maturity in organic-rich source rocks." Vibrational Spectroscopy 87 (2016): 14-19. (Year: 2016).*
Aloulou, F., "Shale gas and tight oil are commercially produced in just four countries", U.S. Energy Information Administration, Independent Statistics Analysis, 2, 2015, 2 pages.
Beyssac, O. et al., "Raman spectra of carbonaceous material in metasediments: A new geothermometer", Journal of Metamorphic Geology, 2002, 20(9), pp. 859-871.
Diessel, C. F. K., et al., "Coalification and Graphitization in High-Pressure Schists in New Caledonia", Contributions to Mineralogy and Petrology, 1978, 68(1), pp. 63-78.
Hood, A. et al., "Organic Metamorphism and the Generation of Petroleum", AAPG Bulletin, 1975, 59(6), pp. 986-996.
Hutton, A. et al., "Chemical and Petrographic Classification of Kerogen/Macerals", Energy Fuels, 1994, 8, pp. 1478-1488.
Landis, C. A., "Graphitization of Dispersed Carbonaceous Material in Metamorphic Rocks", Contributions to Mineralogy and Petrology, 1971, 30(1), pp. 34-45.
Marshall, A. O. et al., "Raman Spectroscopic Investigations of Burgess Shale-Type Preservation: A New Way Forward", Palaios, 2012, 27(5), pp. 288-292.
Wikipedia Article, "Raman Spectroscopy" [https://en.wikipedia.org/wiki/Raman_spectroscopy], accessed Dec. 28, 2018, 11 pages.
Liu et al., "Sample maturation calculated using Raman spectroscopic parameters for solid organics: Methodology and geological applications", Chinese Science Bulletin, Geochemistry (Apr. 2013) vol. 58, pp. 1285-1298.

(56) References Cited

OTHER PUBLICATIONS

International Search Report and Written Opinion for corresponding PCT Application Serial No. PCT/US2019/030035, dated Aug. 2, 2019, 12 pages.
Definition of "maturity" as retrieved from https://www.glossary.oilfield.slb.com/Terms/m/maturity.aspx (Year: 2017).

* cited by examiner

FIG. 3.1
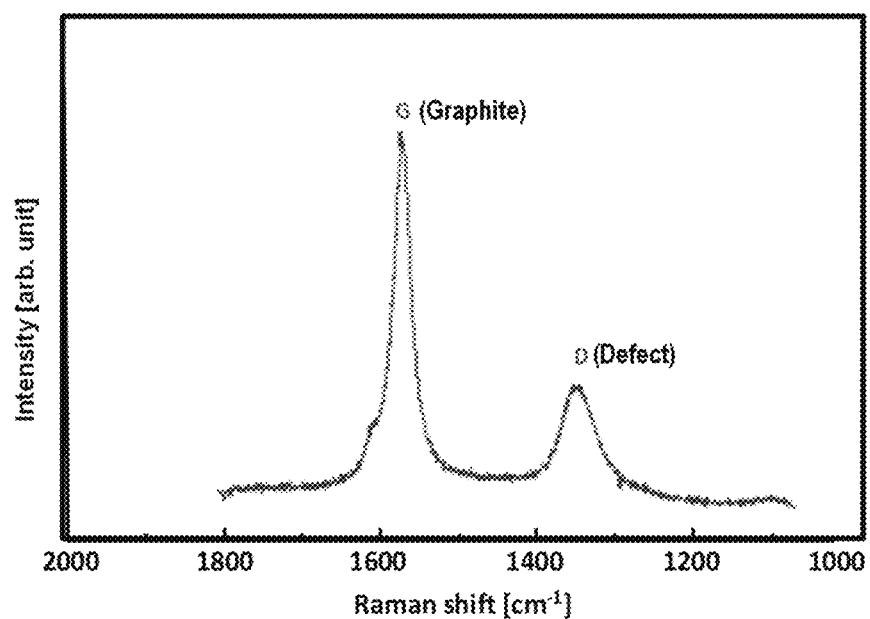
FIG. 3.2
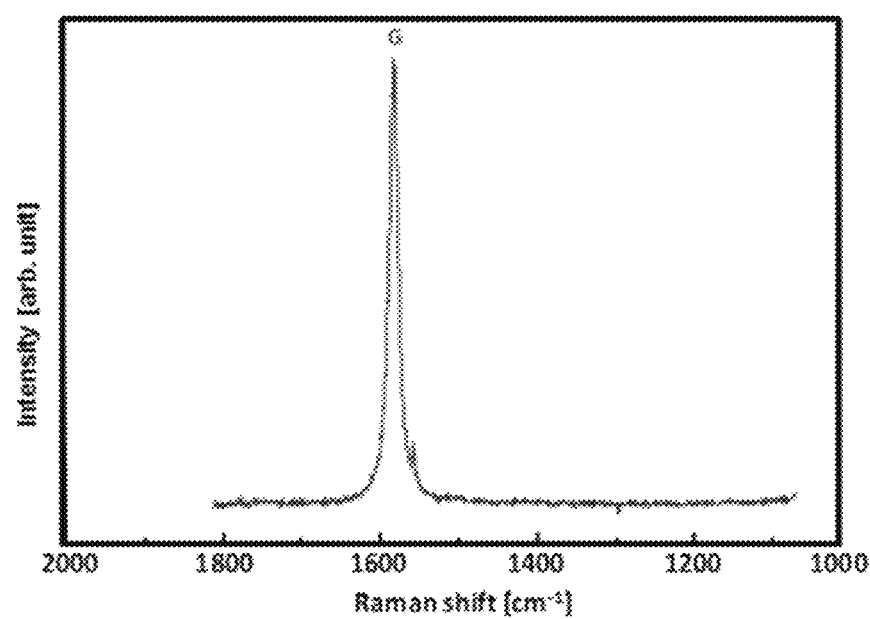

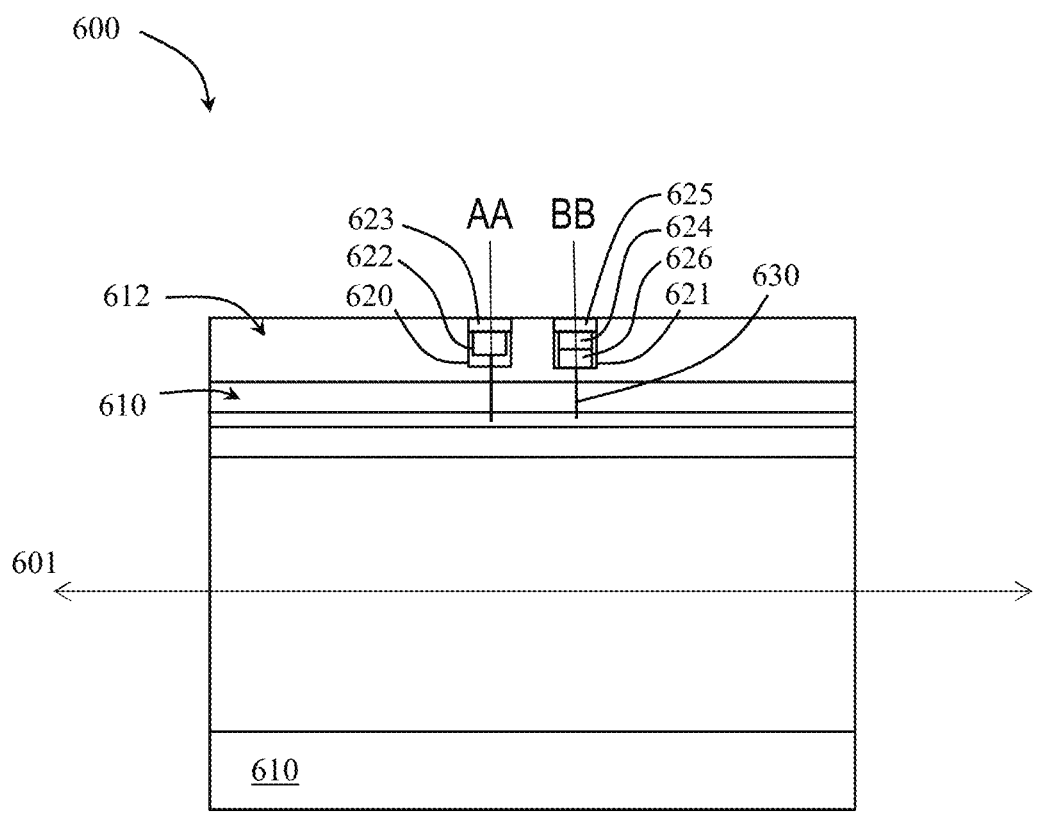
FIG. 6.1

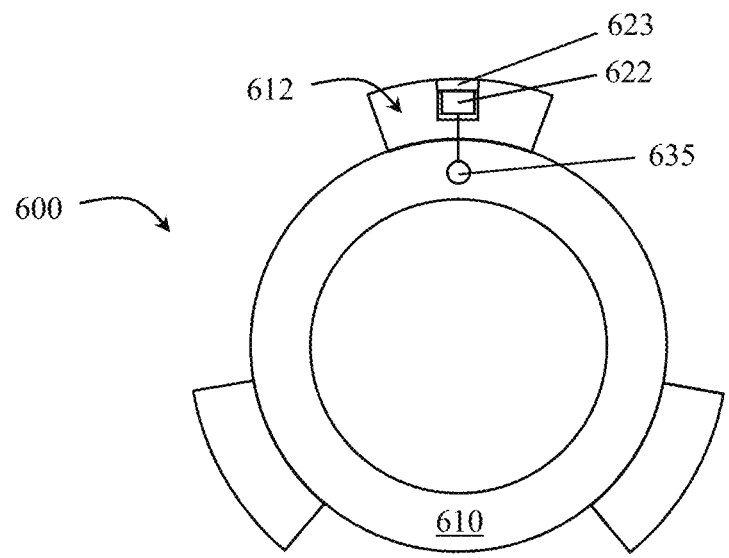
FIG. 6.2
Section AA
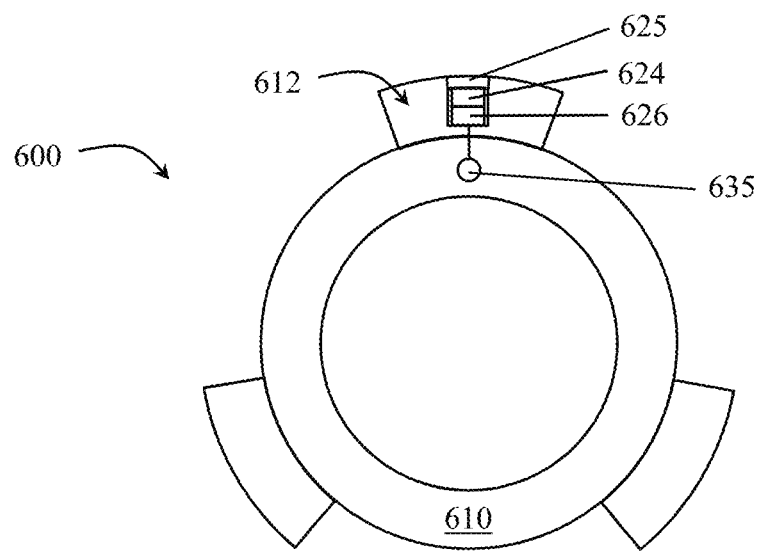
FIG. 6.3
Section BB

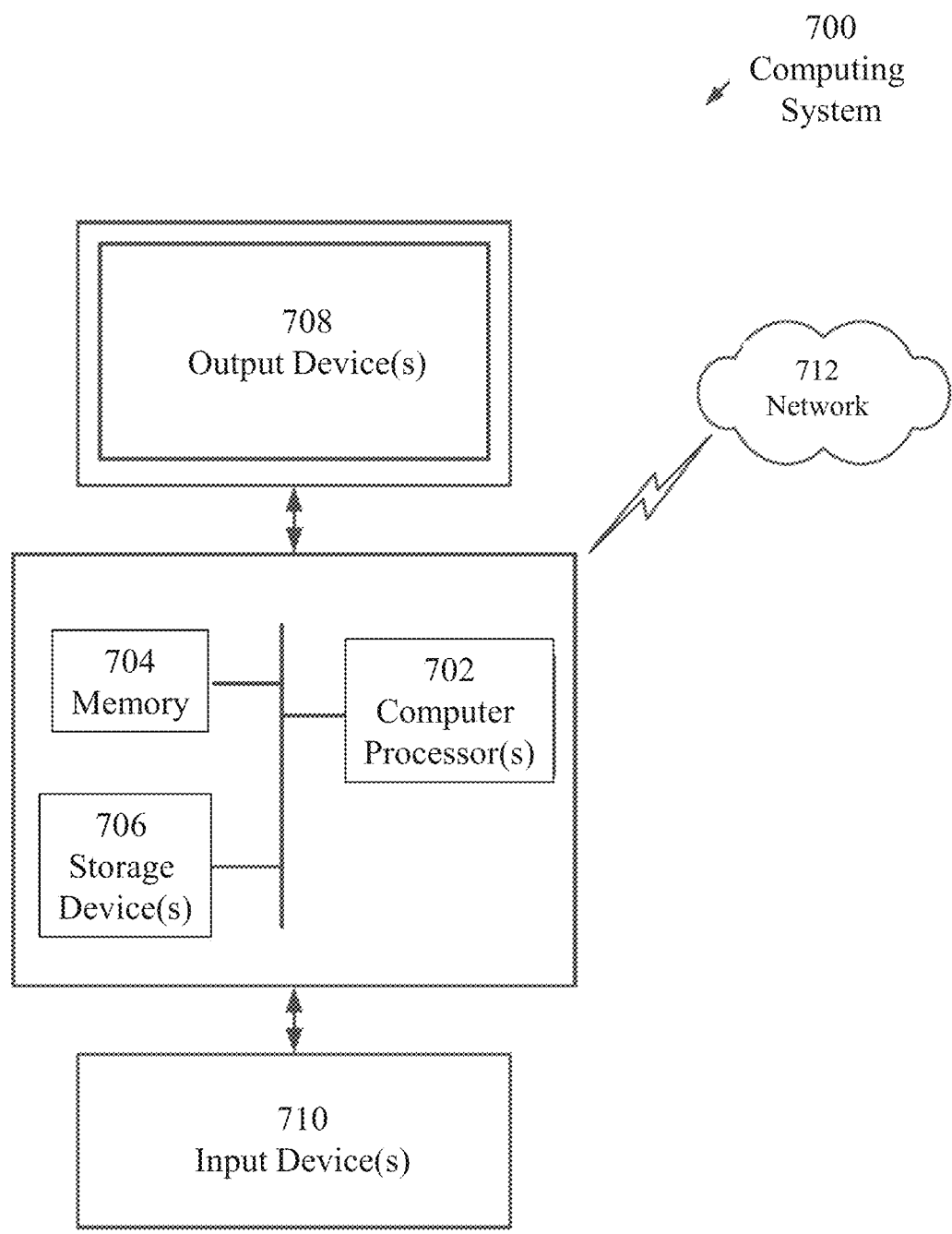

METHOD FOR PERFORMING RAMAN SPECTROSCOPY WITHIN A LOGGING WHILE DRILLING INSTRUMENT

CROSS REFERENCE

This Application is a Divisional Application of co-pending U.S. patent application Ser. No. 15/978,322, filed on May 14, 2018, now U.S. Pat. No. 11,530,611, and entitled "METHOD FOR PERFORMING RAMAN SPECTROSCOPY WITHIN A LOGGING WHILE DRILLING INSTRUMENT" the entirety of which is incorporated herein by reference.

BACKGROUND

Knowledge of the maturity of kerogen (e.g. in organic-rich mudstones such as shales or in tight carbonates) plays an important role in reservoir characterization of unconventional plays, as it provides information of the hydrocarbon type that is to be expected in the reservoir.

Kerogen thermal maturity can be determined by vitrinite reflectance measurements on the respective macerals in kerogen. However, significant expertise is required for this method, which is also very labor intensive. In addition, in formations where vitrinite is not present, such as in formations deposited earlier than the Devonian period which lack the respective marcerals, no such determination can be made.

Another established method to estimate thermal maturity is the so-called Rock-Eval pyrolysis, where formation samples are subject to programmed heating and the amount of hydrocarbons generated from decomposition of kerogen is measured. Formations that have only low amounts of organic material or those who are highly mature do not show accurate estimates using this approach. Other methods, such as X-ray diffraction and high-resolution transmission electron microscopy are commonly used to study graphitization of organic matter. However, these methods work better in the high maturity region, which is not of interest for studying kerogen in the oil and gas windows.

Most common maturity estimations are based on complex laboratory methods, which require the kerogen to be isolated from the rock matrix or the sample to be crushed. Such methods are generally destructive and time intensive.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments of the present disclosure relate generally to downhole tools having a tool body with an outer diameter equal to a borehole diameter, at least one cavity formed in and opening to an outer surface defining the outer diameter of the tool body, a light source, a filter, and a light detector mounted in the at least one cavity, and a window disposed at the opening of the at least one cavity, wherein the window encloses the cavity.

In another aspect, embodiments of the preset disclosure relate generally to methods that include taking a Raman spectroscopy measurement of a formation from within a borehole extending through the formation, generating a Raman spectrum from the Raman spectroscopy measurement, and determining kerogen maturity in the formation from the Raman spectrum.

In yet another aspect, embodiments of the present disclosure relate generally to methods that include drilling a borehole through a formation, taking a Raman spectroscopy measurement within the borehole during drilling to obtain a Raman spectrum, determining kerogen maturity in the formation from the Raman spectrum, and geo-steering the drilling of the borehole based on the kerogen maturity.

Other aspects and advantages of the claimed subject matter will be apparent from the following description and the appended claims.

BRIEF DESCRIPTION OF DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIGS. 3.1 and 3.2 are Raman spectra of kerogen and graphite, respectively, showing the characteristic signal peaks;

FIGS. 6.1 to 6.3 are alternative cross-sectional views of a downhole tool having a Raman spectroscopy measurement system integrated therein in accordance with embodiments of the present disclosure; and FIG. 7 is a schematic showing an example of a computer system for executing methods in accordance with the present disclosure.

DETAILED DESCRIPTION

In one aspect, embodiments disclosed herein relate generally to analysis of hydrocarbon-bearing formations, such as shale. Hydrocarbon containing shale is formed from the debris of organic matter and is composed of thin-grain clay and silt-like particles that formed rock layers with very low permeability. Carbon matter, primarily kerogen, may be diffused within the shale matrix. Kerogen, the insoluble portion of the organic material, thermally decomposes into oil, wet gas, dry gas, and nonhydrocarbons such as $CO_2$, $N_2$, and $H_2S$. The solid-state metamorphic transformation of kerogen may also be referred to as graphitization. As kerogen evolves through thermal maturity, its chemical bonds continue to break and its hydrogen and heteroatom content slowly degrade, which leads to pure carbon in the form of graphite. The extent and the possibility of generating hydrocarbons depends on the amount and type of kerogen and the magnitude and duration that heat and pressure were applied. Graphitization, or thermal maturity, may be measured using analytical techniques such as X-ray diffraction, high-resolution transmission electron microscopy (HRTEM), and maximum temperature during RockEval pyrolysis. However, these techniques are either destructive or inapplicable to shale. X-ray diffraction, for example, requires the extraction of organic matter using acid dissolution of the carbonates and silicates.

According to embodiments disclosed herein, analysis of the maturity of kerogen contained in a formation may be performed using Raman spectroscopy in different formation types, including but not limited to, shale, sandstone, limestone and other carbonates.

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Figure 1:
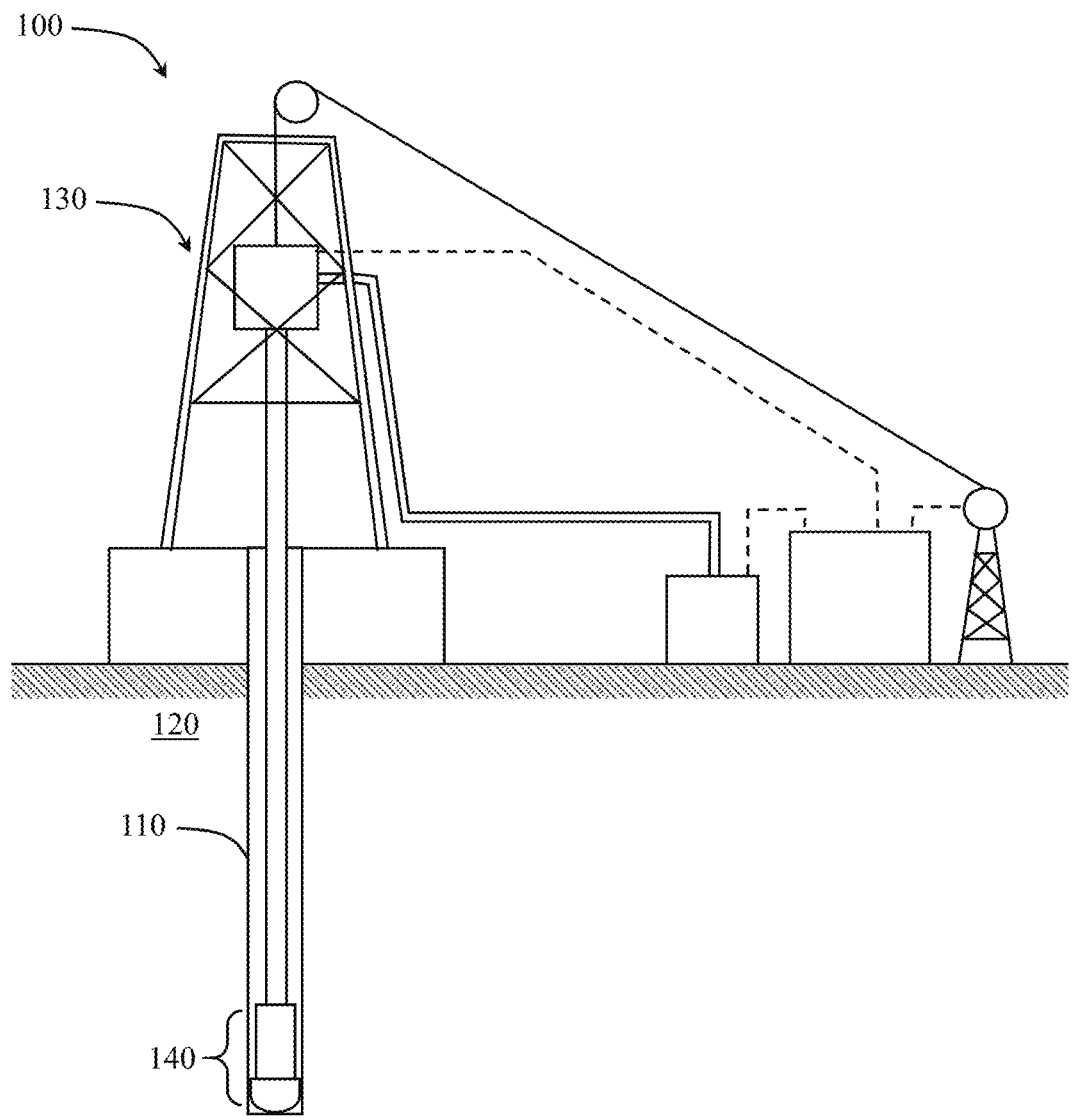
FIG. 1 shows an example of a drilling system according to embodiments of the present disclosure.

FIG. 1 shows a simplified example of a drilling system 100 drilling a well 110 into a formation 120. Equipment 130 for drilling the formation is located on the surface of the formation 120 and extends into the well 110 and typically includes a turn table, a kelly, drill pipe, a drill collar, a drill bit, a mud pump, shale shaker, etc. A bottom hole assembly 140 is made of equipment used in cutting and/or abrading the formation to form the well borehole and is disposed at an axial end of the drill string. A bottom hole assembly may include a drill bit, a reamer, one or more stabilizers, and/or other hole opening equipment.

According to embodiments of the present disclosure, a Raman spectroscopy system optimized for the determination of kerogen maturity may be integrated within one or more components of a bottom hole assembly. For example, a Raman spectroscopy system may be integrated into an outer surface of a reamer as part of a well drilling bottom hole assembly. In this way, continuous measurements of kerogen maturity within the borehole can be obtained while drilling.

Figure 2:
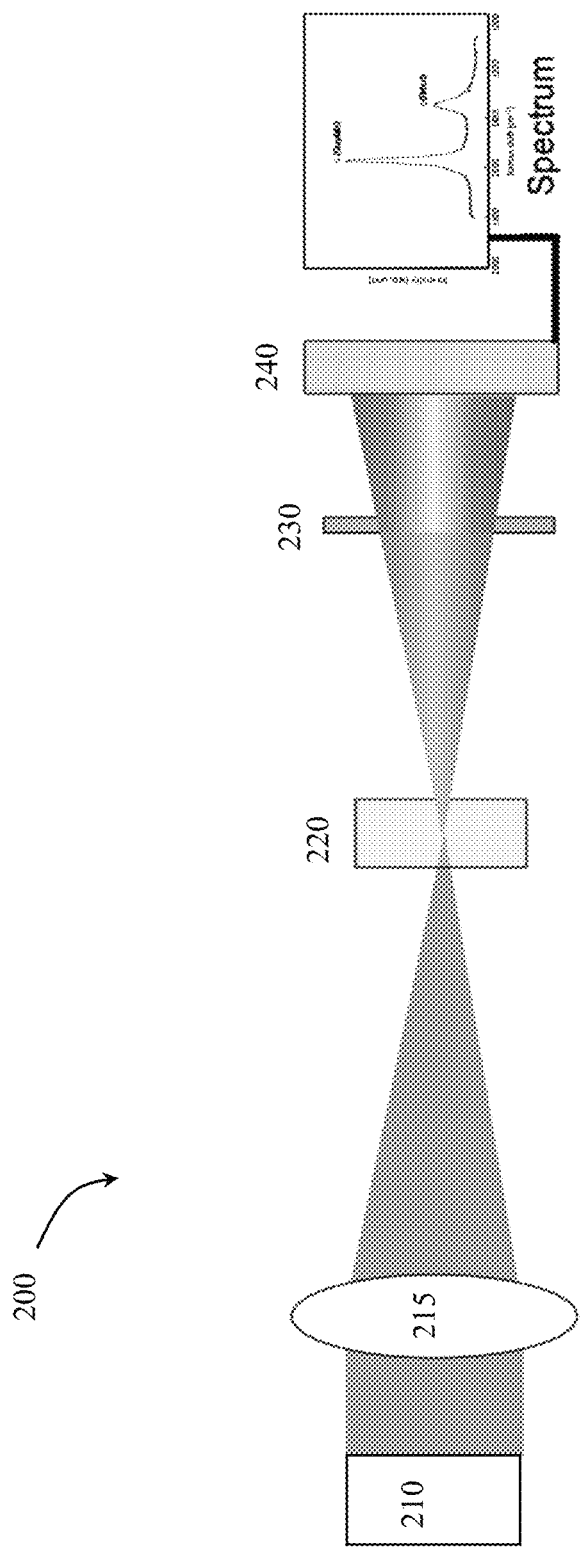
FIG. 2 is a schematic showing the optical elements for a Raman spectroscopy system in accordance with embodiments of the present disclosure.

As illustrated in FIG. 2, a Raman spectroscopy system 200 may generally include a light source 210, a light path to and from a sample 220, a light filter 230, and a frequency sensitive light detection device 240. The light source 210 may be a laser such as a solid-state laser. In some embodiments, the light source 210 may direct light through a lens 215 and monochromator to illuminate the sample 220 with light of a suitable wavelength. A monochromator may act as a type of filter and may be a prism, diffraction grating, or other wavelength separating device. After hitting the sample 220, elastic scattered radiation at the wavelength corresponding to the laser line (Rayleigh scattering) may be filtered out by a light filter 230, such as a notch filter, edge pass filter, or a band pass filter, while the rest of the collected light (Raman scattering) is dispersed onto the frequency sensitive light detection device 240. The frequency sensitive light detection may be accomplished with a grating spectrometer and charge coupled device (CCD) imaging device. The intensity of detected Raman scattering may be plotted versus the Raman shift (the difference between the measured frequency of Raman scattering and the light hitting the sample) in terms of wavenumber to generate a Raman spectrum.

A first-order Raman spectrum of kerogen has two broad peaks. A defect (D) band appears at ~1350 cm$^{-1}$ and is associated with lattice defects and discontinuities of the carbon matter structure. A graphite (G) band appears at ~1600 cm$^{-1}$ and is indicative of well-ordered, graphite-like carbon structures in the kerogen. The similarity to graphite for mature kerogen material can be seen in FIGS. 3.1 and 3.2, where the Raman spectrum of kerogen (FIG. 3.1) is compared with the Raman spectrum of graphite (FIG. 3.2). With increasing maturity (from increase in temperature and pressure) the kerogen becomes more and more structured. In immature carbonaceous material, deconvolution of the bands can show more vibrational defect modes. These defects were found to be attributed to in-plane heteroatoms and tetrahedral carbons that are released in the early part of the maturation process.

Figure 4:
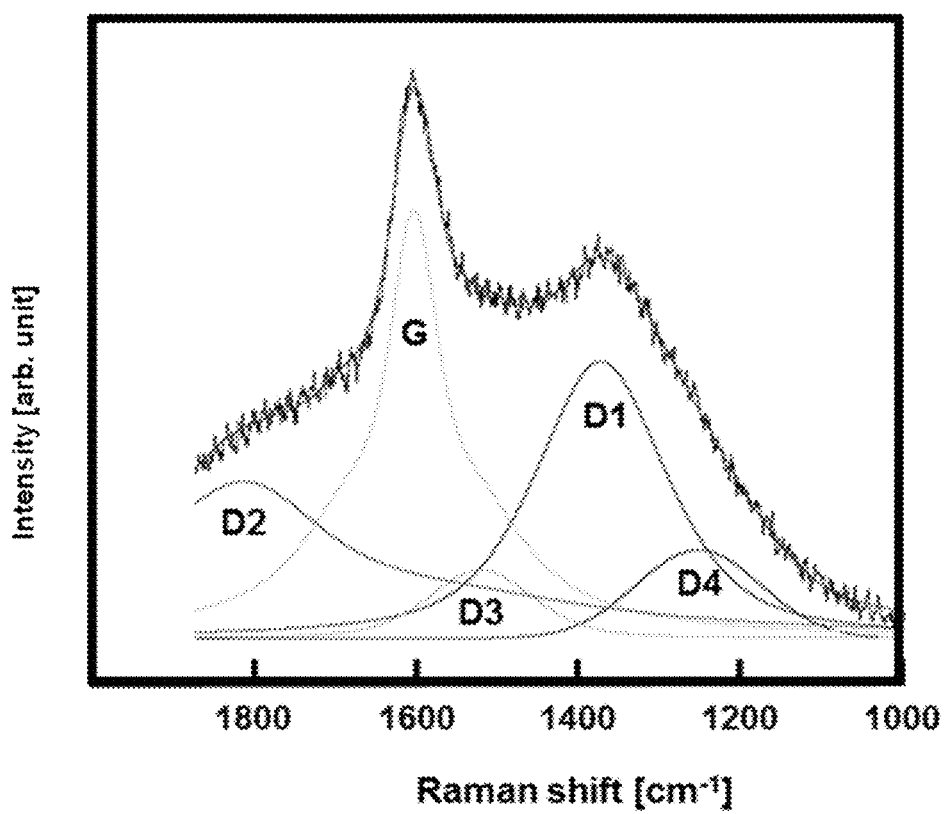
FIG. 4 shows peak deconvolution applied to a Raman spectrum from kerogen according to embodiments of the present disclosure.

A peak fitting procedure shown in FIG. 4 may be applied to accurately derive the D and G peak positions, which in turn may be used to calculate a maturity indicator. In some embodiments, a method for determining shale maturity may be based on the peak separation of the D and G peaks in a Raman spectrum, referred to as the Raman Band Separation (RBS), where $$RBS = W_G - W_D$$

$W_G$ is the G peak position and $W_D$ is the D peak position. The three quantities, $W_G$, $W_D$, and RBS are wavenumbers expressed in units of cm$^{-1}$.

Another method for determining shale maturity may be based on a formulation using the ratio of the area under the D peak, $A_D$, to the area under the G peak, $A_G$, and is referred to as the Band Area Ratio, D/G, where $$D/G = \frac{A_D}{A_G}$$

The two peak areas may be obtained via a peak deconvolution, as illustrated in FIG. 4. In the peak deconvolution shown in FIG. 4, four individual D peaks have been assumed. $A_G$ is the area under the single G peak indicated, while $A_D$, can be the area under the primary D peak, $D_1$, or the sum of the areas of $D_1$ and one or more of the secondary D peaks, $D_2$, $D_3$ and $D_4$.

Based on a correlation derived from a database or other recording of Raman and vitrinite reflectance measurements, this maturity indicator may then be converted into vitrinite reflectance equivalents, an industry accepted standard measurement for maturity of organic-rich mudstones. For example, correlation between Raman measurements and vitrinite reflectance equivalents may be created from organic-rich mudstones with known vitrinite reflectance, where the Raman—vitrinite reflectance correlation may be recorded and used in characterizing kerogen maturity. In some embodiments, the correlation between Raman measurements and vitrinite reflectance may be obtained by fitting a curve to particular Raman and vitrinite reflectance data obtained from a variety of formation samples taken from different regions, ages, mineralogies and maturity levels. The advantage of the Raman based method is that it does not require the presence of vitrinite macerals. The method therefore allows maturity determination of pre-Devonian formations, which lack vitrinite and therefore do not allow maturity determination by standard vitrinite reflectance measurements.

Conventionally, vitrinite reflectance is used as a maturity indicator for organic matter. However, vitrinite reflectance determinations are prone to human error due to the optical validation and use a significant amount of acquisition time. Further, averaging could give false maturity readings due to the heterogeneity of shale samples. More significantly, this technique cannot be applied when vitrinite macerals are absent, as in some shale formations.

Raman spectroscopy, on the other hand, offers nondestructive, rapid measurements that can aid in shale identification and characterization of organic and inorganic molecules. Raman scattering is a function of the molecular vibrations and symmetries of chemical bonds and thus can provide a fingerprint for identification purposes. Further, Raman spectroscopy may offer less averaged information with a high spatial resolution of up to 1 μm. Thus, a measurement of kerogen maturity based on Raman spectroscopy may more accurately characterize shale deposits, which may provide more cost-effective production from shale formations.

A method for determining shale maturity based on the Raman spectrum of kerogen has been described in co-pending International Application No. PCT/US2018/018869, filed Feb. 21, 2018, which is fully incorporated herein by reference. Generally, such method may include determining the RBS of a Raman spectrum generated from Raman spectroscopy measurements of a sample, correlating the determined RBS to a known vitrinite reflectance equivalent, and then using the vitrinite reflectance equivalent as a maturity indicator of the sample. Raman—vitrinite reflectance correlation may include, for example, collecting Raman spectra and vitrinite reflectance measurements of samples, plotting the Raman measurements as a function of measured vitrinite reflectance, and fitting a curve to the plotted points to form a fitted curve graph, e.g., using a best-fit regression. Such a curve may be used later in correlating a Raman measurement to a vitrinite reflectance, which may include finding a vitrinite reflectance value along a first axis (the x- or y-axis) of the fitted curve graph that corresponds to the point on the fitted curve having a Raman measurement of a target sample (where the value of Raman measurements is provided along the second axis (either the x- or y-axis) of the fitted curve graph).

According to embodiments of the present disclosure, a Raman spectroscopy system may be integrated into an outer surface of a downhole tool in a back-scatter configuration, such that the Raman spectroscopy system may collect Raman measurements of a borehole wall while the tool is within the borehole. A Raman spectroscopy system may be integrated in a downhole tool in a back-scatter configuration sufficient for collecting Raman measurements of samples downhole, within a borehole, by mounting components of a Raman spectroscopy system within a radially outermost surface of the tool or other outer surface of the tool known to contact the borehole wall. For example, a downhole tool may have the components of a Raman spectroscopy system disposed in a single cavity formed in an outer surface of the downhole tool or in multiple cavities formed in an outer surface of the downhole tool, where the multiple cavities are in close enough proximity to allow the cooperation of the components therein in taking a Raman back-scatter measurement.

Figure 5:
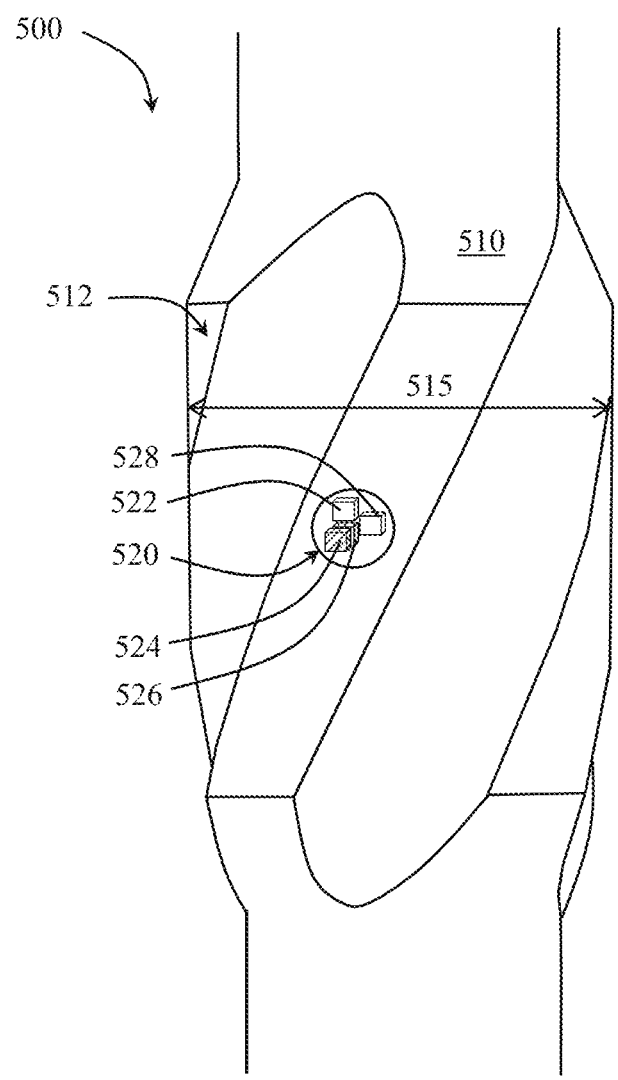
FIG. 5 shows a downhole tool according to embodiments of the present disclosure.

FIG. 5 shows an example of a downhole tool 500 according to embodiments of the present disclosure. The tool 500 includes a tool body 510 having an outer diameter 515, at least one cavity 520 formed in and opening to an outer surface defining the radially outermost diameter 515 of the tool body 510, and a light source 522, a filter 524, and a light detector 526 mounted in the at least one cavity 520. A filter used in a Raman spectroscopy system according to embodiments of the present disclosure may be a device that separates and/or filters bands of wavelength radiation, including but not limited to, monochromators (e.g., prisms and diffraction grating), notch filters, and band pass filters. The light source 522 may be, for example, a solid-state laser, and the light detector 526 may be a charge coupled device.

The light source 522 and light detector 526 may be configured to take a back-scatter measurement in order to analyze a sample located outside of the cavity, such as a borehole wall in which the downhole tool 500 may be disposed. In the back-scatter configuration, the filter 524 may be positioned in front of the light detector 526 (closer to the cavity opening than the light detector) so the back-scattered radiation may pass through the filter 524 before reaching the light detector 526. FIG. 5 shows a perspective view of the back-scatter configuration, where the light source 522 and light detector 526 are positioned in a side-by-side arrangement (although not necessarily touching each other), and where the filter 524 is positioned on top of and covers the light detector 526 (although not necessarily touching). A window may be disposed at the opening of the cavity 520 to enclose the contents (components of a Raman spectroscopy system) of the cavity 520 therein.

According to embodiments of the present disclosure, a Raman spectroscopy system may further include one or more cooling devices, such a Peltier cooler or other refrigeration device, which may be used to cool one or more components of the Raman spectroscopy system, such as the light source and/or light detector. For example, in the tool 500 shown in FIG. 5, a cooling device 528 may be enclosed within the cavity 520 to keep the light source 522 and light detector 526 cool.

The tool 500 shown in FIG. 5 is an integral blade stabilizer, where the tool body 510 includes a plurality of blades 512 extending radially outward from a longitudinal axis to the outer diameter 515. A cavity 520 is formed in at least one of the plurality of blades 512 such that the cavity 520 opens to a radially outermost surface on the tool 500 (at its outer diameter 515). By integrating a Raman spectroscopy system at the radially outermost surface on a downhole tool, the Raman spectroscopy system may be adjacent to (either in contact with or in close proximity to) a borehole wall as the downhole tool moves through the borehole.

Components of a Raman spectroscopy system may be disposed in a single cavity, such as shown in FIG. 5, where a light source, filter and light detector in a Raman spectroscopy system may be mounted in a single enclosed cavity. As mentioned above, in some embodiments, components of a Raman spectroscopy system may be disposed in different cavities. For example, a light source may be mounted in a first enclosed cavity, and a filter and light detector may be mounted in a second enclosed cavity.

FIGS. 6.1-6.3 show an example of a downhole tool having components of a Raman spectroscopy system disposed in different cavities formed along a radially outermost section of the tool. FIG. 6.1 is a longitudinal cross-sectional view of a downhole tool 600; FIG. 6.2 is a radial cross-sectional view of the tool 600 along radial plane AA shown in FIG. 6.1; and FIG. 6.3 is a radial cross-sectional view of the tool 600 along radial plane BB shown in FIG. 6.1.

The tool 600 has a tool body 610 with blades 612 extending radially outward from the tool's longitudinal axis 601. Two cavities 620, 621 are formed in an outer surface of a blade 612, where each cavity 620 has components of a Raman spectroscopy system therein. The cavities 620 are positioned in a line along the blade 612 parallel with the longitudinal axis 601, where the cavities 620 are separated from each other but close enough together to allow cooperation of the Raman spectroscopy components in taking Raman measurements. In a first cavity 620, a light source 622 may be enclosed therein by a window 623 mounted at the opening to the cavity. A filter 624 and a light detector 626 may be enclosed within a second cavity 621 by a window 625 mounted at the opening to the cavity. The window material may be transparent to light to allow Raman spectroscopy measurements outside of the cavity while also protecting the contents of the cavities from borehole fluid and other borehole debris.

In this arrangement, the light source 622 and light detector 626 are configured to take back-scatter measurements, which may be used to analyze a borehole wall as the tool 600 is moved through the borehole. According to other embodiments, the light source, filter and light detector may be placed within the same cavity within a tool blade, where the light source is placed next to the filter and light detector in order to preserve the back-scatter configuration.

Raman spectroscopy measurements may be sent to the surface of a borehole via a telemetry system. For example, as shown in FIGS. 6.1-6.3, electrical signals representing the Raman spectroscopy measurements may be sent through wires 630, where the wires 630 may run through wire channels 635 through the downhole tool 600. According to embodiments of the present disclosure, Raman spectroscopy measurements may be sent through wires or may be transmitted through wireless transmission devices from downhole to the surface of the borehole. In some embodiments, Raman spectroscopy measurements may be stored in a recording subsystem within the downhole tool.

Boreholes for oil and gas can be very high temperature depending on their depth and the local thickness of Earth's crust and proximity to magma bearing structures. Therefore, the devices of Raman spectroscopy systems of the present disclosure may be able to operate at elevated temperatures. For example, a light source and light detector in a Raman spectroscopy system may be based on solid state technology (e.g., a light source may be a solid-state laser and a light detector may be a charge coupled device (CCD), which is also a solid-state device). The band gap separation used in the functioning of solid state devices can be bridged by the effect of elevated temperature, resulting in failure of the solid-state device. Therefore, cooling of the light source and/or light detector may be needed, which may be provided by a Peltier cooler or other refrigeration device. The cooler may be placed within the same cavity within the tool blade as the light source and/or light detector. If the light source and detector are within the same cavity, then a single cooler may be applied to both devices.

The blades 612 of the downhole tool 600 shown in FIGS. 6.1-6.3 may be the same diameter as a borehole before reaming and may have rounded edges without cutting features. In this case, the blade 612 may exclude borehole fluid such as drilling mud from between the blade 612 and the borehole wall, but it may not cut down to fresh rock on the borehole wall. Alternatively, the blades can have a larger diameter than a borehole before reaming, where the outer surface of the blade may include cutting features such as the PDC inserts. In this case, the blade may both exclude borehole fluid from between the blade and the borehole wall and cut fresh rock on the borehole wall.

According to embodiments of the present disclosure, a Raman spectroscopy system may be integrated in various types of downhole tools, similar to that described above with respect to the tools shown in FIGS. 5 and 6. For example, a Raman spectroscopy system may be integrated into a Logging While Drilling (LWD) instrument for use in oil and gas wells, a Measuring While Drilling (MWD) instrument, a reamer (e.g., an on-gauge roller reamer or a reamer at a bit), a fixed diameter hole opener, or other part of a bottom hole assembly. By integrating a Raman spectroscopy system within a reamer or other part of a well drilling bottom hole assembly as described herein, continuous measurements of kerogen maturity within the borehole can be obtained while drilling.

Since shale maturity is a key indicator of the quality of a reservoir rock, it is advantageous to measure this property in situ while drilling a well. Well Logging While Drilling is known to provide many benefits for formation evaluation; the primary benefit being the premium value of data obtained and analyzed during the drilling process, while the trajectory or other aspects of the well can be adjusted. By measuring the shale maturity during the drilling process, one can make real-time decisions that affect the drilling operation and thus improve the recoverable oil or gas from the well. Analysis of shale maturity from core samples is too late to affect the drilling operation, while analysis of shale maturity from drilling cuttings can be sufficiently delayed preventing optimum placement of a well. However, Logging While Drilling provides timely formation evaluation data.

An important aspect of good quality Raman spectroscopy measurements is sample cleanliness. The measurement is very shallow, so it is sensitive to whatever material is immediately in front of the light source and the light detector (illustrated in FIG. 2). In a borehole environment, the borehole is contaminated by various borehole fluids including drilling mud, cuttings, and formation fluids like oil, gas or brine. For a successful Raman spectroscopy measurement of the maturity of kerogen in the rock matrix, drilling mud and other contaminants from the surface of the rock matrix to be analyzed are excluded from the target sample.

During a drilling operation and near to the drill bit, the newly drilled formation is as clean as can be hoped for without a separate cleaning process at the surface. Furthermore, drilling is often accompanied by a reaming process to bring the borehole into gauge, i.e., bring the borehole to the specified diameter. This reaming activity provides an opportunity for performing the Raman spectroscopy measurement on freshly cut rock that has momentarily been excluded from borehole fluids. Embodiments disclosed herein combines the instrumentation for performing the Raman spectroscopy with the structure of a reamer or other downhole tool having an outer surface at gauge with a borehole to allow downhole Raman spectroscopy measurements of a borehole wall without interference from borehole fluids. The Raman spectroscopy system may be in communication with the telemetry and recording subsystem of a Logging While Drilling (LWD) or Measurement While Drilling (MWD) system.

In such manner, the Raman spectroscopy system may provide data in real-time to the surface via an LWD or MWD telemetry system, so that drilling decisions may be based on the information coming from the Raman spectroscopy system. In this way, geo-steering of a well may be performed using kerogen maturity, so that the well path can be optimized for maximum oil or gas recovery.

A method of geo-steering a well using real-time kerogen maturity data according to embodiments of the present disclosure may include drilling a borehole through a formation, taking a Raman spectroscopy measurement within the borehole during drilling to obtain a Raman spectrum, determining kerogen maturity in the formation from the Raman spectrum, and geo-steering the drilling of the borehole based on the kerogen maturity. Kerogen maturity may be determined from a newly obtained Raman spectrum by correlating the Raman band separation and/or band area ratio of the newly obtained Raman spectrum with a vitrinite reflectance equivalent using previously collected Raman spectrum and correlating vitrinite reflectance measurements (e.g., which may be plotted and curve-fitted).

The Raman spectroscopy measurement may be taken with a back-scatter Raman spectroscopy measurement system incorporated within a surface of a bottom hole assembly used to drill the borehole. In other words, the Raman spectroscopy system may be integrated into a surface of the bottom hole assembly known to be in contact with the borehole. The Raman spectroscopy measurement may be sent from within the borehole to a surface of the formation via a telemetry system.

In some methods, the kerogen maturity may be determined from the Raman spectrum by determining a Raman band separation between a graphite peak at approximately 1600 $cm^{-1}$ and a defect peak at approximately 1350 $cm^{-1}$ on the Raman spectrum and correlating the Raman band separation with a known maturity indicator derived from previously collected and correlated Raman and vitrinite reflectance measurements. A Raman band separation between a defect peak and a graphite peak on the Raman spectrum may be correlated with a vitrinite reflectance equivalent from a database (or other recorded Raman—vitrinite reflectance correlated data) to determine the kerogen maturity in the formation, e.g., by fitting a curve to plotted Raman and vitrinite reflectance measurements collected from formation samples and referring to the curve to associate a newly measured Raman spectra with a vitrinite reflectance equivalent. In some methods, determining kerogen maturity may include determining a band area ratio of the area under one or more defect peaks on the Raman spectrum to the area under a graphite peak on the Raman spectrum and correlating the band area ratio with a known maturity indicator. As described above, the band area ratio may be the sum of the areas under a primary defect peak and one or more secondary defect peaks over the area under the graphite peak on the Raman spectrum, or the band area ratio may be the area under a primary defect peak over the area under the graphite peak on the Raman spectrum.

According to embodiments of the present disclosure, a method for determining kerogen maturity in a formation may include scraping a section of a downhole formation, taking the Raman spectroscopy measurement of the section of the formation before the section of the formation is exposed to borehole fluids, and generating a Raman spectrum from the Raman spectroscopy measurement.

Embodiments of the present disclosure may be implemented on a computing system, including any combination of mobile, desktop, server, embedded, or other types of hardware. For example, as shown in FIG. 7, the computing system 700 may include one or more computer processor(s) 702, associated memory 704 (e.g., random access memory (RAM), cache memory, flash memory, etc.), one or more storage device(s) 706 (e.g., a hard disk, an optical drive such as a compact disk (CD) drive or digital versatile disk (DVD) drive, a flash memory stick, etc.), and numerous other elements and functionalities. The computer processor(s) 702 may be an integrated circuit for processing instructions. For example, the computer processor(s) may be one or more cores, or micro-cores of a processor configured to perform methods described above, including correlating Raman spectroscopy measurements with kerogen maturity indicators.

The computing system 700 may also include one or more input device(s) 710, such as a touchscreen, keyboard, mouse, microphone, touchpad, electronic pen, or any other type of input device. Further, the computing system 700 may include one or more output device(s) 708, such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system 700 may be connected to a network 712 (e.g., a local area network (LAN), a wide area network (WAN) such as the Internet, mobile network, or any other type of network) via a network interface connection (not shown). The input and output device(s) may be locally or remotely (e.g., via the network 712) connected to the computer processor(s) 702, memory 704, and storage device(s) 706. Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments of the disclosure. Further, one or more elements of the aforementioned computing system 700 may be located at a remote location and connected to the other elements over a network 712.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. It is the express intention of the applicant not to invoke 35 U.S.C. § 112 (f) for any limitations of any of the claims herein, except for those in which the claim expressly uses the words 'means for' together with an associated function.

What is claimed:
1. A method, comprising:
cutting a fresh surface in a wall of a borehole extending through a formation with one or more blades of a downhole tool;
taking a Raman spectroscopy measurement of the fresh surface from within the borehole extending through the formation before the fresh surface is exposed to borehole fluids with a Raman spectroscopy measurement system, the Raman spectroscopy measurement system including:
a light source disposed in a first cavity in an outer surface of a blade of the one or more blades, wherein the first cavity is enclosed by a first window flush with the outer surface of the blade;
a filter disposed in a second cavity in the outer surface of the blade, wherein the second cavity is enclosed by a second window flush with the outer surface of the blade; and
a light detector disposed in the second cavity;
generating a Raman spectrum from the Raman spectroscopy measurement; and
determining kerogen maturity in the formation from the Raman spectrum.
2. The method of claim 1, further comprising:
determining a Raman band separation between a defect peak and a graphite peak on the Raman spectrum; and correlating the Raman band separation with a vitrinite reflectance equivalent to determine the kerogen maturity in the formation.

3. The method of claim 1, wherein the Raman spectroscopy measurement is a back-scatter measurement.

4. A method, comprising:
drilling a borehole through a formation;
cutting a fresh surface in a wall of the borehole with one or more blades of a downhole tool;
taking a Raman spectroscopy measurement of the fresh surface within the borehole during the drilling to obtain a Raman spectrum before the fresh surface is exposed to borehole fluids with a Raman spectroscopy measurement system, the Raman spectroscopy measurement system including:
 a light source disposed in a first cavity in an outer surface of a blade of the one or more blades, wherein the first cavity is enclosed by a first window flush with the outer surface of the blade;
 a filter disposed in a second cavity in the outer surface of the blade, wherein the second cavity is enclosed by a second window flush with the outer surface of the blade; and
 a light detector disposed in the second cavity;
determining kerogen maturity in the formation from the Raman spectrum; and
geo-steering the drilling of the borehole based on the kerogen maturity.

5. The method of claim 4, wherein the Raman spectroscopy measurement is sent from within the borehole to a surface of the formation via a telemetry system.

6. The method of claim 4, wherein the Raman spectroscopy measurement system is a back-scatter Raman spectroscopy measurement system.

7. The method of claim 4, wherein determining the kerogen maturity comprises:
determining a Raman band separation between a graphite peak at approximately 1600 $cm^{-1}$ and a defect peak at approximately 1350 $cm^{-1}$ on the Raman spectrum; and
correlating the Raman band separation with a known maturity indicator.

8. The method of claim 4, wherein determining the kerogen maturity comprises:
determining a band area ratio of the area under one or more defect peaks on the Raman spectrum to the area under a graphite peak on the Raman spectrum; and
correlating the band area ratio with a known maturity indicator.

9. The method of claim 8, wherein the band area ratio is the sum of the areas under a primary defect peak and one or more secondary defect peaks over the area under the graphite peak on the Raman spectrum.

10. A method, comprising:
deploying a downhole tool into a borehole extending through a formation, wherein the downhole tool comprises:
 a tool body one or more blades extending radially from the tool body;
 a first cavity formed in an outer surface of a blade of the one or more blades, wherein a first window encloses the first cavity and is flush with the outer surface of the blade;
 a light source mounted in the first cavity;
 a filter mounted in the at least one a second cavity formed in the outer surface of the blade, wherein a second window encloses the second cavity and is flush with the outer surface of the blade; and
 a light detector mounted in the second cavity, wherein the light source and the light detector are configured to rake back-scatter measurements;
cutting a fresh surface in a wall of the borehole with the downhole tool with the one or more blades;
taking a Raman spectroscopy measurement of the fresh surface from within the borehole with the downhole tool to obtain a Raman spectrum before the fresh surface is exposed to borehole fluids;
determining kerogen maturity in the formation from the Raman spectrum; and
geo-steering drilling of the borehole based on the kerogen maturity.

11. The method of claim 10, wherein the downhole tool is a Logging While Drilling instrument for use in oil and gas wells.

12. The method of claim 10, wherein at least one of the first cavity or the second cavity comprises a cooling device enclosed therein.

13. The method of claim 10, wherein the downhole tool is part of a bottom hole assembly.

14. The method of claim 10, wherein the one or more blades have a larger outer diameter than a diameter of the borehole.

15. The method of claim 10, wherein the light source is a solid-state laser.

16. The method of claim 10, wherein the filter is a prism or diffraction grating.

17. The method of claim 10, wherein the light detector is a charge coupled device.

* * * * *